US011419971B2

(12) United States Patent
Banko

(10) Patent No.: US 11,419,971 B2
(45) Date of Patent: Aug. 23, 2022

(54) OCULAR SURGICAL WORK TIP ADAPTER

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 0 days.

(21) Appl. No.: 15/687,762

(22) Filed: Aug. 28, 2017

(65) Prior Publication Data
US 2019/0060534 A1    Feb. 28, 2019

(51) Int. Cl.
*A61M 1/00* (2006.01)
*A61M 39/10* (2006.01)
*A61M 3/02* (2006.01)
*A61F 9/007* (2006.01)

(52) U.S. Cl.
CPC .......... *A61M 1/774* (2021.05); *A61M 1/7411* (2021.05); *A61M 3/0283* (2013.01); *A61M 39/10* (2013.01); *A61F 9/00745* (2013.01); *A61M 2039/1038* (2013.01); *A61M 2039/1077* (2013.01); *A61M 2210/0612* (2013.01)

(58) Field of Classification Search
CPC .. A61M 1/0047; A61M 1/0033; A61M 1/008; A61M 3/0283; A61M 2210/0612; A61F 9/00736; A61F 9/008; A61F 9/00745; A61B 17/32002
USPC .......................................................... 604/22
See application file for complete search history.

(56) References Cited

U.S. PATENT DOCUMENTS

| | | | | |
|---|---|---|---|---|
| 3,088,323 | A | * | 5/1963 | Welkowitz ............ G01L 9/0052 73/849 |
| 3,710,781 | A | * | 1/1973 | Hutchins, IV ....... A61B 5/0215 600/488 |
| 3,776,238 | A | * | 12/1973 | Peyman .............. A61F 9/00763 606/171 |
| 3,805,793 | A | * | 4/1974 | Wright ............. A61B 17/32053 606/29 |
| 3,815,604 | A | * | 6/1974 | O'Malley ............. A61B 18/12 606/171 |
| 4,210,146 | A | * | 7/1980 | Banko ................. A61F 9/00763 606/171 |
| 4,386,927 | A | * | 6/1983 | Eichenbaum ....... A61F 9/00736 604/541 |
| 4,504,264 | A | * | 3/1985 | Kelman ............. A61F 9/00745 604/35 |
| 4,513,745 | A | * | 4/1985 | Amoils ............... A61F 9/00763 606/171 |
| 4,548,205 | A | * | 10/1985 | Armeniades ............. A61B 3/16 600/561 |
| 4,678,459 | A | * | 7/1987 | Onik ................ A61B 17/32002 604/22 |
| 4,819,635 | A | * | 4/1989 | Shapiro ............... A61F 9/00763 600/565 |

(Continued)

*Primary Examiner* — Nathan R Price
*Assistant Examiner* — Mark A Igel
(74) *Attorney, Agent, or Firm* — Leason Ellis LLP

(57) ABSTRACT

An adapter for a surgical hand piece with a single lumen work tip converts the handpiece to infusion/aspiration (I/A) cleanup of lens epithelial cells in the capsular bag of the eye a patient after phacoemulsification. The adapter is in the form of a sleeve whose proximal end is to be joined to the distal end of work tip. The sleeve also has at least one aspiration hole located toward the distal end of the sleeve.

9 Claims, 8 Drawing Sheets

(56) References Cited

U.S. PATENT DOCUMENTS

| | | | | |
|---|---|---|---|---|
| 4,919,130 | A * | 4/1990 | Stoy | A61F 2/1664 |
| | | | | 606/107 |
| 5,056,902 | A * | 10/1991 | Chinnock | A61B 34/73 |
| | | | | 359/503 |
| 5,217,465 | A * | 6/1993 | Steppe | A61M 1/84 |
| | | | | 606/1 |
| 5,267,996 | A * | 12/1993 | Fletcher | A61B 5/6848 |
| | | | | 606/17 |
| 5,285,795 | A * | 2/1994 | Ryan | A61B 17/32002 |
| | | | | 606/171 |
| 5,358,473 | A * | 10/1994 | Mitchell | A61F 9/00736 |
| | | | | 604/27 |
| 5,378,234 | A * | 1/1995 | Hammerslag | A61M 25/0662 |
| | | | | 604/95.04 |
| 5,464,389 | A * | 11/1995 | Stahl | A61F 9/00745 |
| | | | | 606/169 |
| 5,514,086 | A * | 5/1996 | Parisi | A61B 17/22012 |
| | | | | 604/35 |
| 5,667,489 | A * | 9/1997 | Kraff | A61F 9/00745 |
| | | | | 604/35 |
| 5,718,677 | A * | 2/1998 | Capetan | A61F 9/00745 |
| | | | | 604/35 |
| 5,782,849 | A * | 7/1998 | Miller | A61B 17/32002 |
| | | | | 606/159 |
| 6,579,270 | B2 * | 6/2003 | Sussman | A61F 9/00736 |
| | | | | 604/27 |
| 6,902,558 | B2 * | 6/2005 | Laks | A61F 9/00709 |
| | | | | 604/521 |
| 7,238,010 | B2 * | 7/2007 | Hershberger | A61B 17/32002 |
| | | | | 417/477.2 |
| 7,959,597 | B2 * | 6/2011 | Baker | A61M 1/774 |
| | | | | 604/28 |
| 8,282,574 | B2 * | 10/2012 | Coonahan | A61B 10/0275 |
| | | | | 600/568 |
| 8,313,501 | B2 * | 11/2012 | Miller | A61B 17/32 |
| | | | | 606/171 |
| 8,545,462 | B2 * | 10/2013 | Ghannoum | A61F 9/00736 |
| | | | | 604/27 |
| 8,641,658 | B1 * | 2/2014 | Banko | A61F 9/00745 |
| | | | | 604/173 |
| 8,657,840 | B2 * | 2/2014 | Palmer | A61B 17/32002 |
| | | | | 606/170 |
| 9,757,536 | B2 * | 9/2017 | Abt | B29C 66/5344 |
| 10,166,317 | B2 * | 1/2019 | Banko | A61F 9/00745 |
| 10,179,068 | B2 * | 1/2019 | Banko | A61F 9/00745 |
| 10,213,533 | B2 * | 2/2019 | Walter | A61F 9/00834 |
| 10,244,931 | B2 * | 4/2019 | Kern | A61M 5/14 |
| 2005/0256462 | A1 * | 11/2005 | Underwood | A61F 9/00736 |
| | | | | 604/264 |
| 2010/0121260 | A1 * | 5/2010 | Ghannoum | A61F 9/00736 |
| | | | | 604/35 |
| 2015/0025451 | A1 * | 1/2015 | Banko | A61M 1/774 |
| | | | | 604/35 |
| 2016/0106580 | A1 | 4/2016 | Banko | |

* cited by examiner

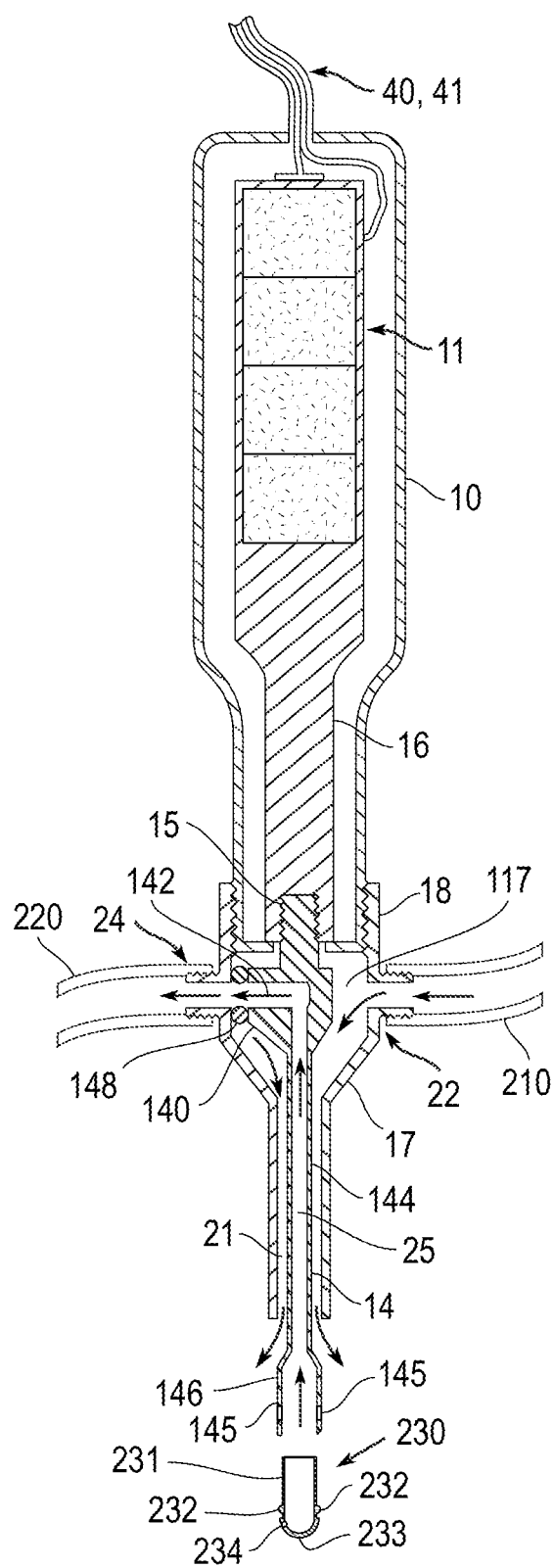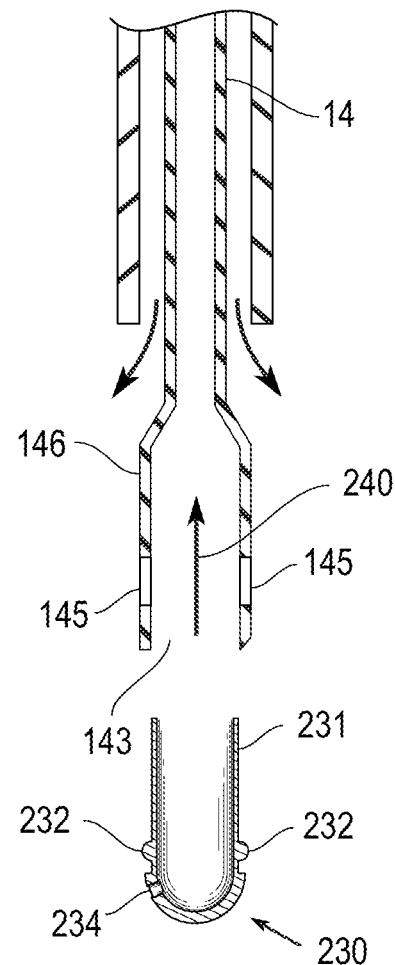
Fig. 5A
Fig. 5B

OCULAR SURGICAL WORK TIP ADAPTER

TECHNICAL FIELD

The present invention is generally directed to hand pieces for ocular surgery, particularly for the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

FIG. 1 depicts one such type of prior art ultrasonic hand piece as shown in U.S. Pat. No. 4,504,264 of Kelman. This hand piece has a housing 10 of, for example, plastic or metal, within which is supported a transducer means 11 for generating mechanical vibrations upon excitation with an alternating-current electrical signal. The transducer 11 is shown as a magnetostrictive transducer with an electrical coil 12 wound about a stack of metal laminations so that longitudinal mechanical vibrations are produced. The transducer can also be of the piezoelectric type. There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is connected, such as by a screw thread, to the narrowed distal end of the connecting body 16 so as to be coupled to the transducer 11. As a result, the work tip is longitudinally vibrated by the transducer. The working tip 14 is an elongated, hollow tip of a suitable metal, such as titanium, that is capable of supporting ultrasonic vibrations. It has a distal end of a desired shape to be placed against the tissue to be removed. The work tip 14 has a base portion 15 in threaded engagement with the distal end of the connecting body 16. The tip 14 can be interchanged by use of the screw threads.

The distal end of the tip 14 is shown surrounded by a sleeve 17, which may be made of a material such as silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric 0-rings 19, 20 on its outer surface. These provide a fluid-tight seal between the connecting body 16 and the transducer means 11. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The hand piece also illustratively has electrical input terminals 40, 41 for applying a suitable electrical signal to the magnetostrictive transducer 11. Cooling water is shown provided inside the housing 10 from an inlet 42 to an outlet 43 and within a chamber between 0-ring 19 and a grommet 50 for circulation around the transducer. This is not always necessary and is not used in most present day hand pieces.

The sleeve 17 around the tip 14 forms a first fluid passage 21 between the tip 14 and the sleeve for an infusion/irrigation fluid. An inlet 22 is provided on the housing or sleeve distally of the 0-ring 20 for supplying the irrigation fluid to the passage 21 from a fluid supply, e.g., a bag of saline solution (not shown).

A passage 23 is formed through the connecting body 16 that is in communication with a central passage 25 of the work tip 14. An outlet 24 on the housing or sleeve receives a suction (aspiration) force that is applied to the passage 23 in the connecting body and the central passage 25 in the work tip. A chamber 31 is formed between the spaced 0-rings 19, 20 on the body 16 and the housing 10, with which the aspiration force from outlet 24 communicates. Thus the aspiration force is from the source (e.g., a suction pump not shown), into the chamber 31 between the 0-rings, through the passage 23 in the connecting body and the passage 25 in the work tip 14. Tissue that is emulsified by the work tip is aspirated from the operating site by the aspiration flow force. In particular, saline solution introduced into the eye through fluid passage 21 and tissue displaced by the vibration force of the tip 14, is drawn into the distal end of passage 25 and passes out of the hand piece through outlet 24. It should be noted that passage 25 is located concentrically within passage 21.

As indicated, other apparatus (not shown) for use with the hand piece include the suction pump for producing the aspiration fluid (suction), the treatment fluid supply (infusion/irrigation fluid, such as a saline liquid), an oscillator for applying an electrical signal to the vibratory structure and control apparatus therefore. All of these are of conventional construction.

Considering now the operation of the hand piece of FIG. 1. When an electrical signal having a frequency of, for example, 40,000 cycles/second is applied to the coil 12 around the magnetostrictive transducer 11, the transducer 11 vibrates longitudinally at 40,000 cycles per second, thereby vibrating the connecting bodies 13, 16 and the work tip 14. Treatment fluid is supplied through inlet 22 and fluid passage 21 to bathe the tissue in the operating site region around the working tip 14. Suction force is applied through inlet 24 and passage 23 to the working tip 14 passage 25 to withdraw the tissue fragmented by the work tip along with some of the treatment fluid.

Instruments of the type described above are often used in cataract surgery in which the eye lens is removed from the eye capsule and an intra-ocular lens (IOL) is then implanted. In such a procedure before the IOL is implanted it has been found to be desirable to cleanup lens substance and lens epithelial cells (LEC's) in the capsular bag of the eye and to remove them. Doing this procedure provides a more stable and long-term fixation for certain types of IOL's in the capsular bag. One manner of accomplishing the cleanup is to use a combination of low force irrigation of the capsular bag interior with a liquid together with the application of low power ultrasonic energy. This dislodges the unwanted cells and substances without damage to the capsular bag. Further, this material can be removed from the capsular bag by the aspiration fluid flow, which also may be reduced in pressure to avoid damage.

In a cleanup procedure it is advantageous if the flow of the irrigation liquid can be made more directional than would be possible using the hand piece with the outer sleeve through which the liquid flows and exits from around the work tip that produces the ultrasonic energy. It is also better if the aspiration force is lower. As a result, typically a different tip from the one illustrated in FIG. 1, which breaks up the tissue, is used for the cleanup. In fact a completely different instrument called an irrigation or infusion/aspiration (I/A)

instrument is often used for this purpose. Such an instrument 90 is illustrated in FIG. 2. It has a handle 91 at one end and a work tip 92 at the other end. An enlarged view of the work tip is shown in FIG. 3. The I/A instrument work tip has concentric infusion and aspiration lumens, and typically has no ultrasonic vibration capability. The infusion fluid enters the work tip at opening 93 and is in an outer concentric lumen so that its flow surrounds the distal part of lumen 95 of the work tip. The aspirated tissue enters a small hole 94 in the distal part and is withdrawn through lumen 95. Thus, when the phacoemulsification has been completed and cleanup is to be started, the surgeon must remove the phacoemulsification tool from the eye. Then the surgeon removes the first or phacoemulsification work tip, replaces it with a different cleanup work tip and then inserts the new work tip or a separate I/A tool 90 is inserted in to the eye. This second insertion into the eye increases the possibilities of infection and trauma. Also, the I/A tool has a disadvantage in that the surgeon would have to keep inserting and withdrawing the ultrasonic work tip and the I/A tool from the eye as the process is completed, because the surgeon cannot be sure that all of the tissue has be broken up until the cleanup process has begun. As a result, this would also subject the patient to the increased possibilities of infection and trauma.

As shown in the present inventor's own U.S. Pat. No. 8,641,658, the surgical instrument may be provided with dual lumens in tubes 132, 134, each of which can alternatively be used for aspiration of emulsified tissue and irrigation of the surgical site. FIG. 4 shows a work tip 130 that can be connected to an ultrasonic energy source 102 of a hand piece by means of a connecting body 204. Two fluid passages 120 and 180 for aspiration or irrigation fluid pass through the connecting body 204. For example the proximal end of passage 120 can be in communication with the irrigation fluid input of the supply line 124 and the proximal end of passage 180 can be in communication with the aspiration fluid of the supply line 164. The distal ends of the two passages 120 and 180 terminate at the distal end of the connecting body 204.

There are threads 182 around the connecting body distal end. A hub 190 is around the proximal ends of the work tip tubes 132 and 134, which are bent so that the proximal ends of their lumens are parallel to the distal ends of the connecting body passages 120 and 180. A collar 194 with internal threads on its open end has its flange end rotatably mounted in a groove 192 in the hub 190. There are mating index pieces, such as mating grooves and ribs or pins (not shown), on the opposing faces of the connecting body 204 distal end and the hub 190 so that the proximal end of the lumen of tube 132 will be aligned with the distal end of connecting body passage 120 and the proximal end of the lumen of tube 134 aligned with the distal end of passage 180.

When the tubes and connecting body are properly aligned the collar 194 is tightened on the connecting body threads 182 and the lumens at the proximal ends of tubes 132 and 134 will be brought into fluid communication with the distal ends of the connecting body passages 120 and 180. 0-rings 193 are provided in the connecting body at the distal ends of passages 120 and 180 to make the communications fluid tight.

Both of the tubes 132 and 134 receive the ultrasonic energy from the source 102 (not shown). A valve (not shown) can be used with the hand piece of FIG. 4 to switch the fluid flow from the sources 124 and 164 to the lumens of tubes 132 and 134 of the integrated work tip. Since both tubes 132 and 134 receive ultrasonic energy the emulsification of tissue and its aspiration can take place through either one in addition to each tube being able to supply irrigation liquid through the different types and shapes of openings at the distal ends of the tubes.

The work tip can be used with only an irrigation/aspiration (I/A) function by turning off the source of ultrasonic energy and only supplying the aspiration and irrigation fluids. Thus, the same instrument can be used for the phacoemulsification function while performing irrigation and aspiration as an operation takes place and also only for I/A functions (no or minimal ultrasonic energy is used) useful for cleaning the capsular bag as described above. This eliminates the need for the surgeon changing instruments and also provides the surgeon with a work tip having two tubes with different shape openings available for both aspiration and irrigation.

Only one of the tubes, e.g., 134, can be used as an I/A work tip. In the oval shaped openings 165 along the tube length can be used alone in the eye capsular bag for the substance and cell cleanup procedure described above. The oval shaped openings 165 allow for both good dispersion of the irrigation fluid or a large area for aspiration of cells and substances dislodged by the irrigation liquid.

While the work tip of U.S. Pat. No. 8,641,658 can use its dual lumen tubes for phacoemulsification and for I/A cleanup thereafter, it would be advantageous if these functions could be provided to a single axial work tip as shown in FIG. 1. In addition, it would be beneficial if phacoemulsification instruments with single lumens could have their operation varied without withdrawing the instrument from the eye and/or diverting the surgeon's attention from the operating site. This would reduce the chances of infection and trauma.

SUMMARY OF THE INVENTION

In accordance with the invention a surgical hand piece is provided that can perform all of the functions of emulsification of tissue and other substances by ultrasonic energy and aspiration of such tissue and substances, as well as reduced pressure irrigation and aspiration of a site that is being worked on in order to clean up the site. The hand piece can be used for surgery on appropriate tissue throughout the body, e.g., neurological tissue and ocular tissue.

The invention provides a surgical phacoemulsification hand piece that has a single axial work tip that is concentric to a surrounding irrigation tube. Thus it can be like the prior art work tip in FIG. 1 or an improved work tip as shown in the present inventor's U.S. Patent Application Publication No. US 2015/0025451 A1, which is incorporated herein by reference in its entirety. The improved design has a disposable work tip so that the entire handpiece need not be sterilized between operations.

During a phacoemulsification procedure, an ultrasonic source in the hand piece causes the single work tip to vibrate and to remove cataract tissue. However, when this is complete, the ultrasonic vibration is ended and an adapter converts the work tip for I/A so that it is adapted to clean up of the capsular bag by changing the configuration of the aspiration opening.

In one embodiment the work tip is removed from the eye and an adapter is placed over it so as to modify the opening. In a second embodiment the adapter is fixed to the work tip and its configuration is changed when I/A clean up is desired. With the second embodiment the adapter can be changed without removing the work tip from the eye. Also, the surgeon can selected one of a variety of adapters such that the aspiration pattern during the cleanup can be selected to suit the circumstances. These different patterns can be achieved without the surgeon having to remove the I/A tool from the eye.

The principles of the invention have numerous advantages. For example, the invention allows a phacoemulsification tool to be converted with an adapter to serve as an I/A clean up tool. Further, an embodiment of the invention allows for the elimination of the need for the surgeon to remove an ultrasonically-driven work tip from the operating site, such as the eye, and to insert a separate work tip or tips having I/A cleanup capability, in order to perform special procedures, such as cortical and lens epithelial cell cleanup. Further, if an I/A tool is used according to the present invention, clean up can be commenced without the surgeon having to divert his attention from the eye.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 5A is a cross-sectional view of a first embodiment of a surgical hand piece with a single axial work tip and an adapter for I/A clean up of a capsular bag of the eye according to the present invention, and FIG. 5B is an enlarged view of the attachment of the adapter to the work tip;

DETAILED DESCRIPTION OF THE INVENTION

FIG. 5A shows an embodiment of a handpiece disclosed in the present inventor's US Patent Application Publication US 2015/0025451 A1, which is incorporated herein by reference in its entirety. This handpiece is shown receiving an adapter 230 according to the present invention. The handpiece uses a number of the components of the prior art type of handpiece described above with respect to FIG. 1. The source of the electro-mechanical energy is shown schematically as transducer 11. This transducer can be either the electromagnetic type or the piezoelectric crystal type. It is preferred, and is conventional, that the output power of the transducer 11 be controlled by electrical signals delivered over wires 40, 41 from a control unit (not shown). These signals allow the ultrasonic power at the work tip distal end 146 to be varied as needed by the surgeon.

Figure 1:
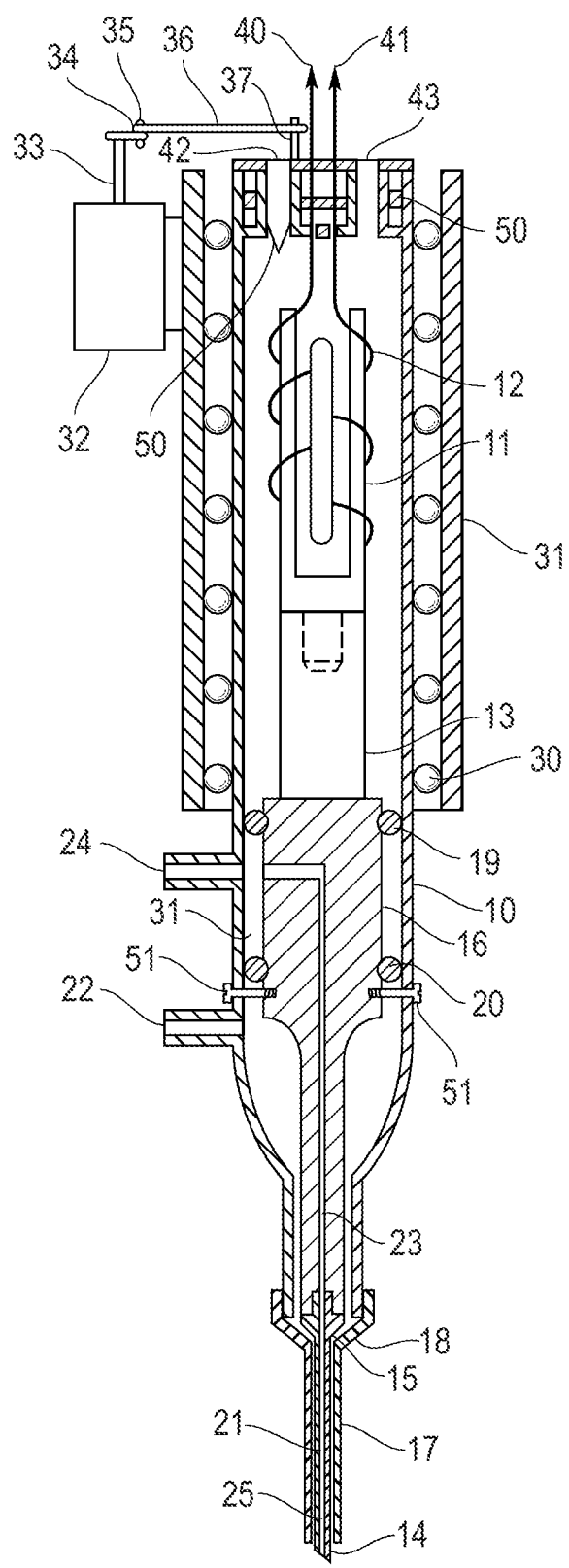
FIG. 1 is a view in partial cross-section of a prior art type of surgical hand piece.
Figure 2:
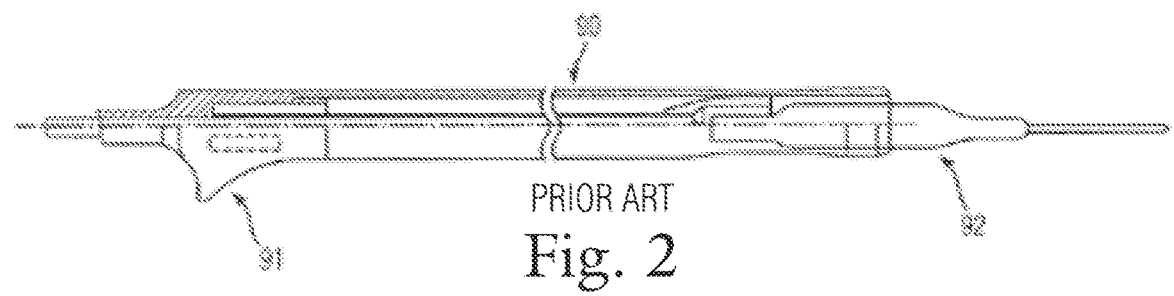
FIG. 2. is a partial cross-sectional view of a prior art irrigation/aspiration instrument with a removable tip.
Figure 3:
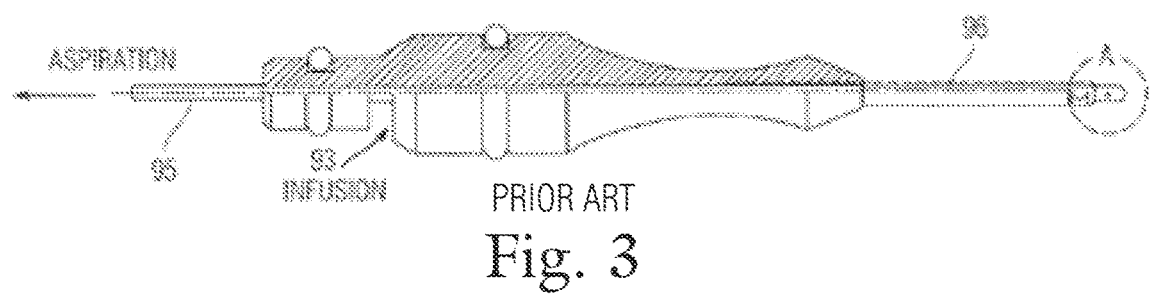
FIG. 3 is a partial cross-sectional enlarged view of the prior art tip for the infusion/aspiration instrument of FIG. 2.
Figure 4:
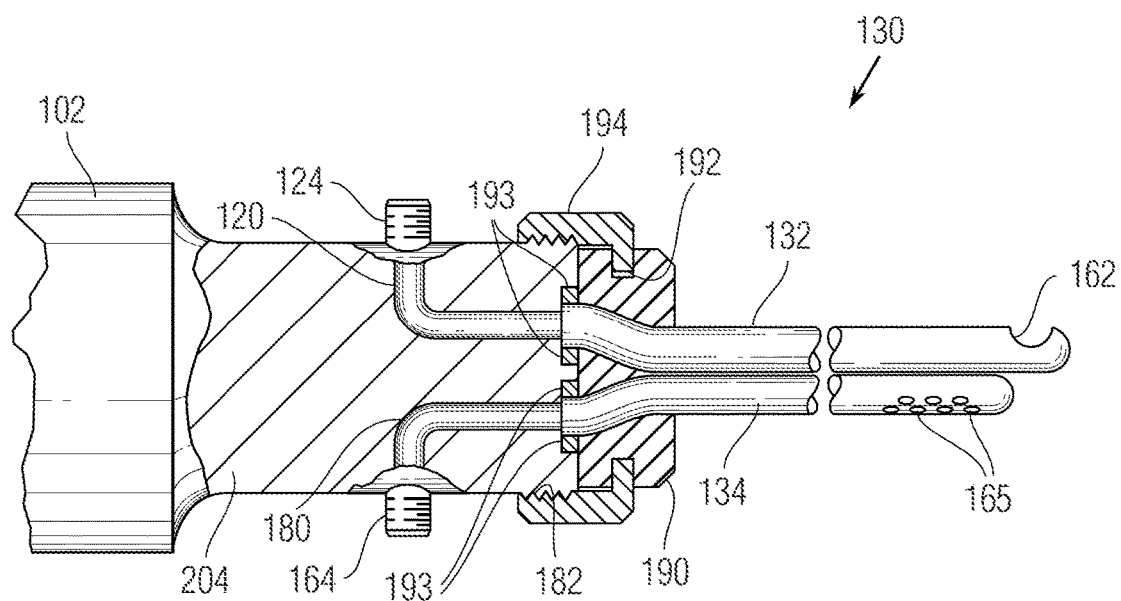
FIG. 4 is cross-sectional view of a prior art dual lumen surgical hand piece.

Connected to the transducer 11 is the connecting body 16. Both the transducer 11 and connecting body 16 are provided in a housing 10. Although not shown for the sake of clarity, the transducer and connecting body are suspended within housing 10 so as to permit the longitudinal vibration of the transducer and connecting body to occur relative to the housing. For example, the 0-rings 19 and 20 shown in FIG. 1 are spaced apart around the connecting body 16 and engage the inner surface of the housing 10.

The work tip 14 has an opening 143 that leads to an axial channel 25 extending from the opening to an enlarged hub 140 at the proximal end of the work tip. Within the hub 140 there is a radial channel 142 that extends from the axial channel 25 to the outer surface of the hub. While the radial channel 142 is shown at a right angle to the axial channel, in fact it can be at any convenient angle that allows it to extend from the axial channel to the outer surface of the hub. A threaded connector 15 extends from the proximal end of the hub and engages the distal end of the connecting body 16.

A sleeve 17, which may advantageously be made of silicone, is provided with a funnel shape so that its proximal end 18 is large enough to encompass the enlarged hub, and still leave space for chamber 117 between the outer surface of the hub and the inner surface of the sleeve. The distal end of the sleeve tapers down around the portion 144 of the work tip beyond the hub, which extends to a flared portion 146 of the work tip which is at the operating or distal end. As a result the axial channel has a larger diameter at the distal end that tapers down to a smaller diameter as it extends through the work tip into the hub 140. The sleeve stops short of the portion 146. The proximal end 18 of sleeve 17 makes a threaded connection with the body 10. Although not shown, a sterile sheet may be fastened to the end 18 and draped over the housing to avoid contaminating the housing during procedures.

Sleeve 17 has a first external connector 22 on its outer surface that is in fluid communication with the chamber 117. A tube 210 carrying irrigation fluid may be connected to connector 22 in order to supply irrigation fluid to chamber 117. Fluid in chamber 117 may flow between the outer surface of work tip portion 144 and the inner surface of sleeve 17 in a channel 21 so as to exit the handpiece just short of the flared portion 146 of the work tip, i.e., at the site of the operation of the handpiece on the patient's tissue. Sleeve 17 also has a second external connector 24 on its outer surface. In the drawing this connector is shown as being on the opposite side of the sleeve from the connector 22. However, in practice this connector can be at any convenient location on the sleeve. A seal piece 148, e.g., an O-ring or other form of seal, connects the radial channel 142 to the second connector 24. A tube 220 provides a suction force (e.g., from a peristaltic aspiration pump) on connector 24. This causes tissue to be drawn into the opening 143 at portion 146 of the work tip, to travel up the axial channel 25 and into the radial channel 142, to pass through the O-ring 148 and the connector 24, and finally to be drawn through tube 220 to the aspiration pump.

In operation the handpiece of FIG. 5A operates similar to other phacoemulsification handpieces. Electrical energy is applied through wires 40, 41, which causes the ultrasonic transducer to vibrate axially at ultrasonic frequencies. The mechanical axial force is transmitted to the connecting body 16, which in turn transmits it to the work tip 14. When the end 146 of the work tip is placed in contact with tissue, e.g., a cataract, the vibration causes the tissue to break up. While this is occurring, irrigation fluid, e.g., saline solution, passes from a source, through tube 210 and connector 22 into chamber 117, along channel 21 and is deposited at the operating site as shown by the arrows 230 in FIG. 5B. At the same time the fragmented tissue is drawn into the opening 143 in portion 146 as shown by arrow 240 in FIG. 5A. It passes up the axial channel 25 into the radial channel 142, through the O-ring 148 and connector 24 to tube 220.

When the handpiece is used in its intended fashion and the procedure is over, the handpieces can be quickly readied for use on another patient without the need for sterilization. In particular, the tubes 210, 220 are disconnected and discarded. Then the sleeve 17 with its sterile sheet at proximal end 18 is unthreaded from the housing 10 and the connecting body 16. Next, the work tip 14 has its threaded connector 15 loosened from connecting body 16. Then the working tip and sleeve 17 are discarded. The work tip and sleeve, as well as each of the sets of tubes are replaced with clean, pre-sterilized parts, and the handpiece is ready for the next use. This is possible because the only parts of the handpiece that come into contact with the aspiration fluid from the patient are the work tip, sleeve and the interior of tube 220. Except for the work tip, the other disposable parts can be made of inexpensive materials, e.g., silicone. Thus, the cost of the replacement parts is not very great.

The work tip of the present invention can be used with only an infusion/aspiration (1/A) function. That is, the source of ultrasonic energy can be turned off or reduced. The aspiration and infusion/irrigation fluids are supplied to the tubes 210 and 220; but, the aspiration force can be lowered, e.g., from 500 mm Hg to 5-10 mm Hg during the cleaning operation so that the posterior capsule tissue at the back of the eye is not drawn into the tube. The irrigation fluid force can also be lowered. However, it is preferable to utilize smaller openings than that of the work tip at 146. One way to accomplish this is to withdraw the work tip from the eye of the patient and to place an adapter 230 over the end of the work tip.

The adapter 230 as best shown in FIG. 5B is a closed end tube with a small opening 234 or series of openings. During clean up, the remaining tissue (i.e., lens epithelial cells) is aspirated through this small hole while irrigation fluid continues to be applied to the site from channel 21. The adapter can be made of metal or soft plastic. If it is made of metal, a soft plastic coating is preferred to avoid damage to the capsular bag of the eye.

The cylindrical proximal end 231 of the adapter is slid into the flared part 146 of the work tip until protrusions 232 on its outer surface engage in recesses 145 within flared part 146. This connection establishes locking engagement between the adapter 230 and work tip 14. This engagement is aided by the suction force within the work tip. Distal end 233 of the adapter is made thicker than the end 231 and surrounds opening 234. The end 231 is also made smooth so as to provide protection against harm to the capsular bag.

Figure 6:
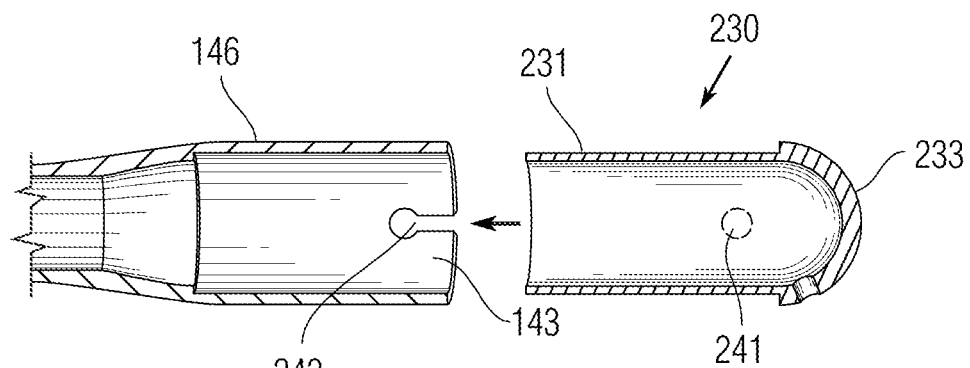
FIG. 6 is an enlarged cross-sectional view of a second embodiment of a work tip and I/A clean up adapter according to the present invention.

FIG. 6 shows an arrangement similar to FIG. 5B, but instead of protrusions 232 and recesses 145, the adapter 230 is fastened to the flared part 146 of the work tip by a protrusion 241 engaging a slot 242 in the flared part 146.

Figure 7A:
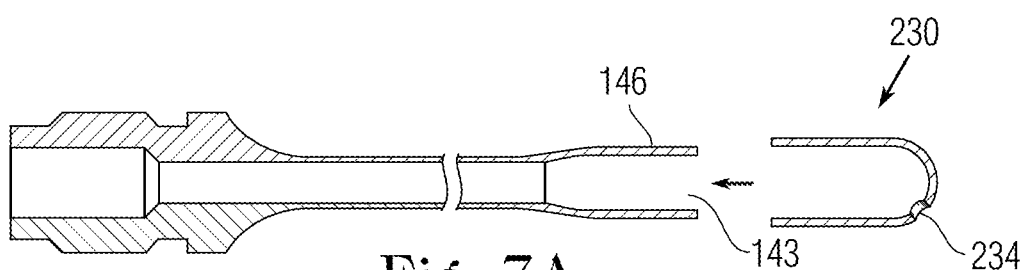
FIGS. 7A and 7B are a cross-sectional view and an enlarged cross-sectional view, respectively, of a third embodiment of a work tip and I/A clean up adapter according to the present invention.
Figure 7B:
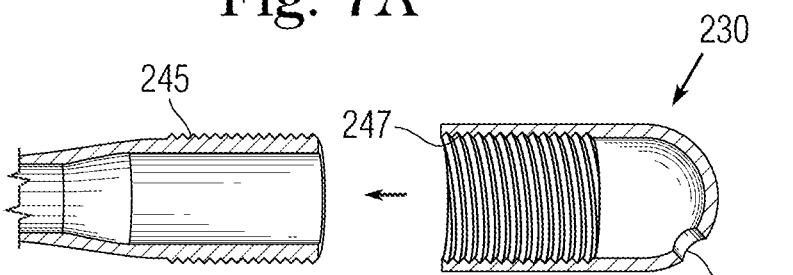

The adapter 230 of FIG. 7A is made larger than the flared part 146 so that the adapter extends over the flared part when installed on the work tip. The flared part has external threads 245 as shown in FIG. 7B which engage internal threads 247 on the adapter 230. This forms the engagement between these parts.

Figure 8A:
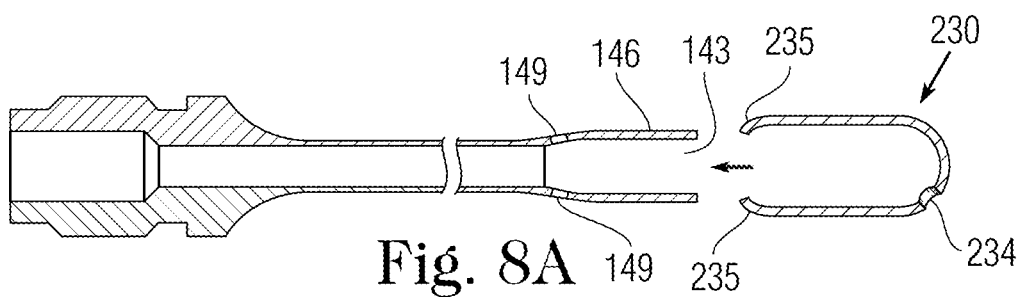
FIGS. 8A and 8B are a cross-sectional view and an enlarged cross-sectional view, respectively, of a fourth embodiment of a work tip and I/A clean up adapter according to the present invention.
Figure 8B:
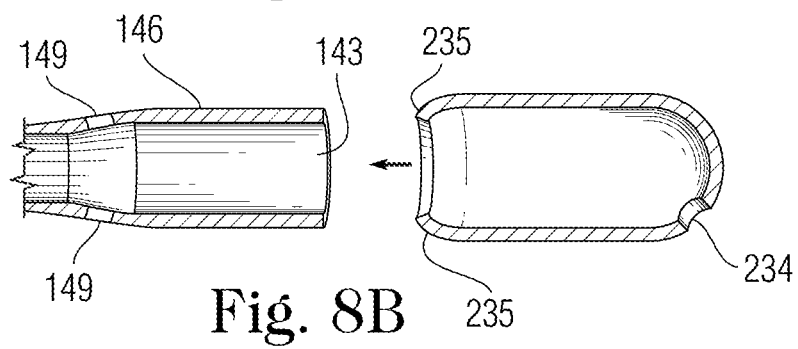

The adapter 230 of FIGS. 8A and 8B is made flexible and slightly larger than the flared part 146. The ends 235 of the adapter bend inwardly. When the adapter is installed it is slid over the flared part, which causes at least the ends to expand outwardly. Once the adapter is nearly over the flared part, the ends 235 of the adapter snap into detents 149 in the exterior surface of the work tip to hold the adapter on the work tip. Note that the adapters shown in FIGS. 7 and 8 do not have the enlarged distal surface 233. Depending on the size (diameter) of the adapter, the surface 233 may not be necessary to protect the capsular bag.

Figure 9A:
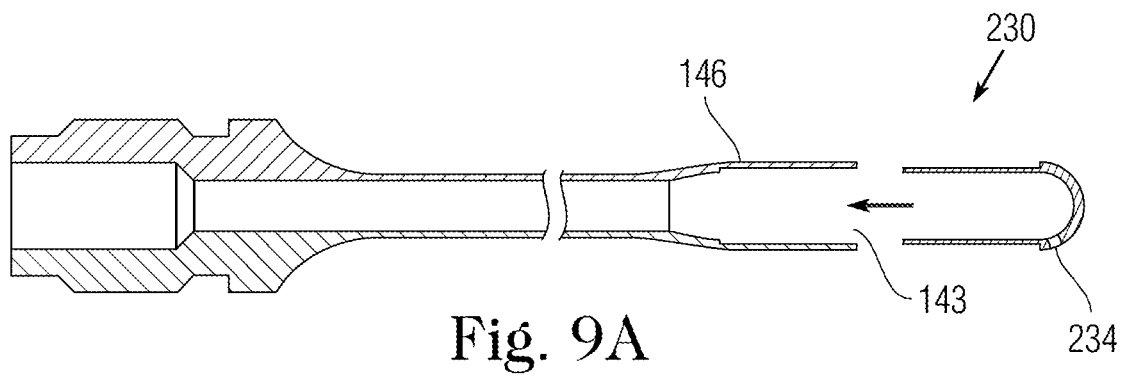
FIGS. 9A and 9B are a cross-sectional view and an enlarged cross-sectional view, respectively, of a fifth embodiment of a work tip and I/A clean up adapter according to the present invention.
Figure 9B:
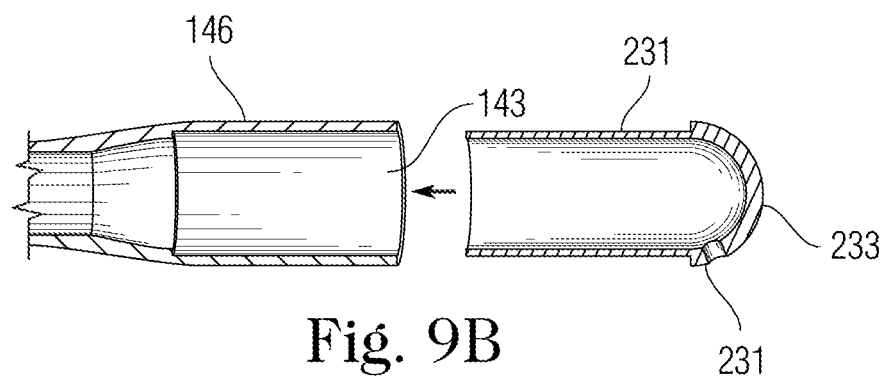

The adapter of FIGS. 9A and 9B resemble that of FIG. 5B in that it is smaller in diameter than the flared part and slides within it. However, instead of protrusions and recesses, this design relies on a press fit between the parts and the aspiration force to hold the adapter on the work tip. Also in this design, the expanded distal part 233 of the adapter is designed to have a thickness that matches that of the flared part so that when joined the two parts have a smooth connection line.

Figure 10:
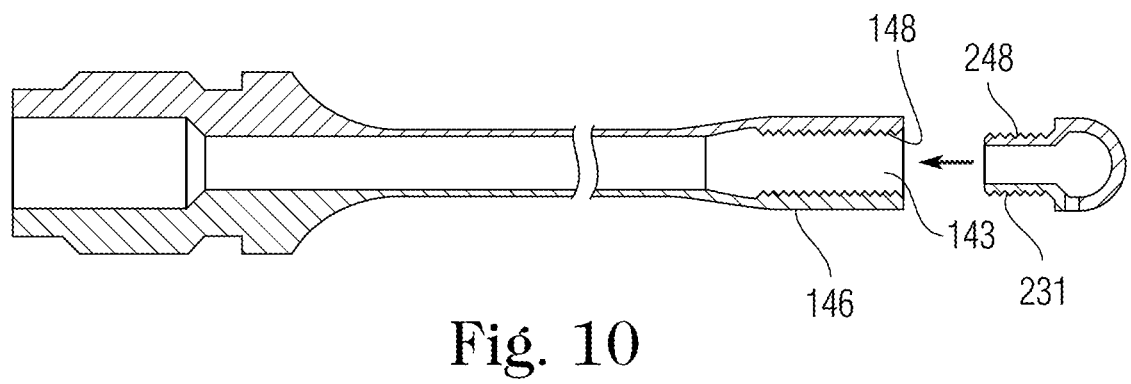
FIG. 10 is a cross-sectional view of a sixth embodiment of a work tip and I/A clean up adapter according to the present invention.

The embodiment of FIG. 10 is the opposite of that in FIG. 7. In particular, the adapter has threads 248 on a reduced diameter portion of its proximal end 231, which end slides within the flared part 146. The threads 248 of the adapter engage threads 148 on the interior of the flared part.

In each of the designs of FIGS. 5-10, the aspiration opening 234 has been shown as a simple hole. However, it should be understood that opening 234 may be a plurality of openings in different patterns, of different sizes and with different shapes. The surgeon will select the adapter to best meet the conditions that present during the surgery.

With the designs of FIGS. 5-10, it is necessary for the surgeon to remove the work tip from the eye of the patient in order to make use of any particular adapter. This of course takes time away from the procedure, exposes the surgical site to infection and/or trauma. Thus, it would be advantageous to be able to engage a clean-up adapter without having to remove the work tip form the eye. Such a design is shown in FIG. 11.

Figure 11:
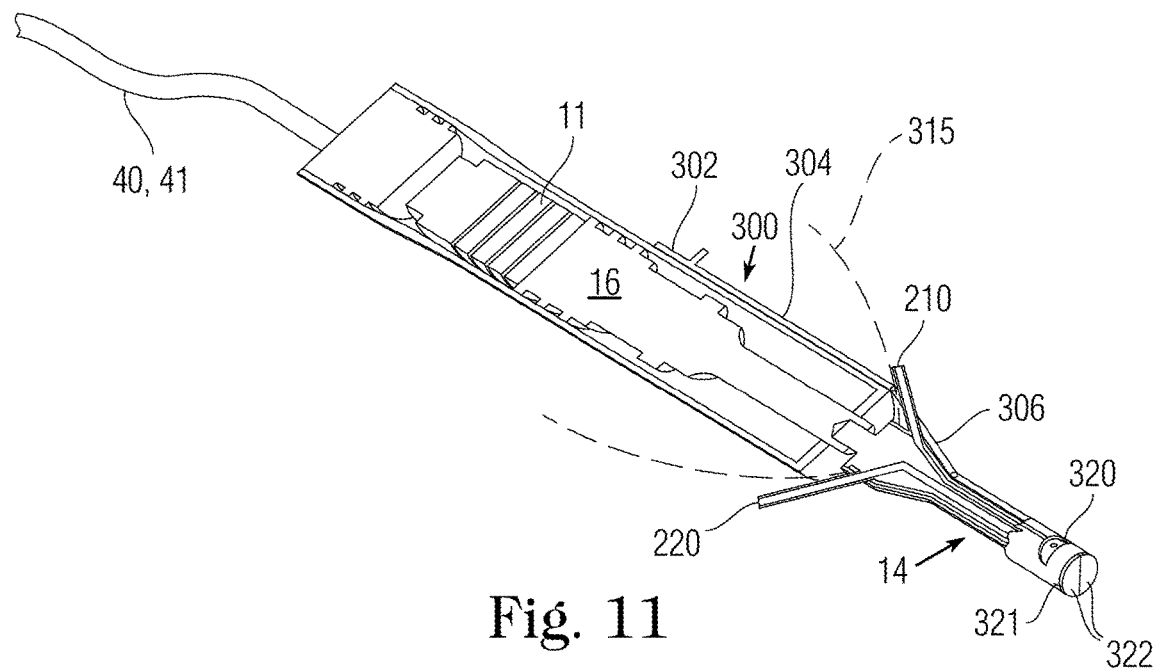
FIG. 11 is a perspective view of a hand piece with a mechanism for sliding a sleeve to change the function of an adapter according to the present invention without removing the work tip from the eye of the patient.

FIG. 11 shows a hand piece with a work tip 14 at the end. Either the irrigation sleeve 17 or an additional sleeve 320 located outside the irrigation sleeve can slide along the work tip. In the embodiment of FIG. 11, the sliding of the sleeve 320 is achieved with a mechanism 300 attached to the exterior of the hand piece. Mechanism 300 includes a finger portion 302. The finger portion is connected to a linear portion 304 that runs along the exterior surface of the hand piece and is slidable with respect to that surface. A slanted portion 306 extends from the linear portion down to the work tip and then connects to sleeve 320. All of the portions of mechanism 300 are slidable with respect to the hand piece. The mechanism 300 is preferably located on the hand piece such that it does not interfere with the irrigation and aspiration tubes and is close to the body of the hand piece. Also, preferably, the pieces 302, 304, 306 and 320 are flexibly joined to each other so that during the sliding motion, they do not extend way from the body of the work piece. Depending on the shape of the hand piece, additional or fewer sections of the mechanism 300 may be used. Also, a sterile sheet 315 is shown attached to the hub of the work tip. A portion or portions of the mechanism would penetrate the sterile sheet, if used, to reach the finger portion 302 on the housing.

When the surgeon completes the emulsification of the cataract and wants to start to clean up the remaining tissue, he or she turns off the ultrasonic energy or reduces it, reduces the force of the irrigation and aspiration fluid flows and uses his or her finger to slide the sleeve 320 forward. This can all be accomplished without removing the work tip from the surgical site within the patient's eye. In general the effect of sliding the adapter is to cause to openings in the work tip to be reconfigured for I/A clean up.

During operations in the eye, sections 306 and 320 may become contaminated. As a result, they may be made detachable from the rest of the mechanism so that they can be discarded after a procedure, as opposed to being sterilized. At the same time the work tip 14 with the attached sterile sheet 315 would be disposed. The mechanism 300 is preferably made of plastic material to save on costs.

Figures 12A, 12B, 12C, 12D:
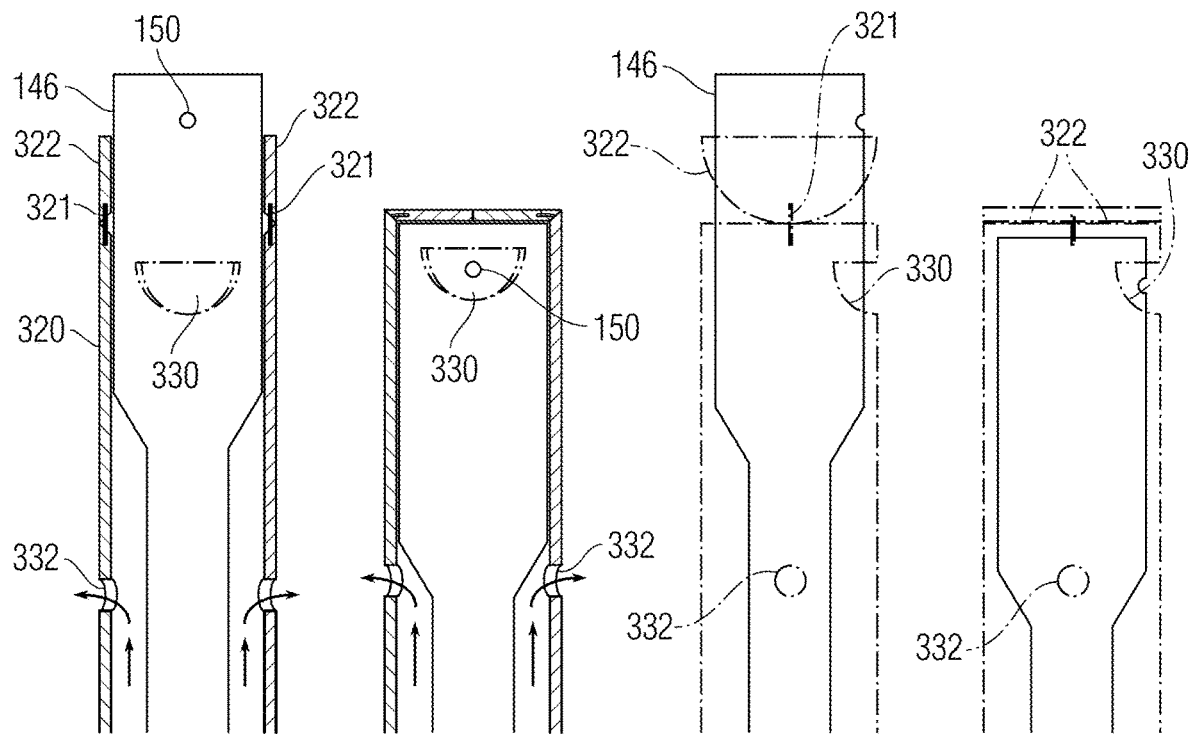
FIG. 12A is a front cross sectional view of an adapter in the form of a hinged sleeve according to the present invention mounted on a work tip in an open position.
FIG. 12B is a front cross sectional view of the adapter of FIG. 12A with the hinge closed.
FIG. 12C is a schematic side view of the adapter of FIG. 12A with the hinge open and FIG. 12D is a schematic side view of the adapter of FIG. 12B with the hinge closed.

FIG. 12A shows a work tip with a flared part 146 in solid line. Sleeve 320 is shown in cross section surrounding it. It will be noted that the work tip has a small opening 150 near its distal end. Further, the sleeve 320 has a hole 332 at a distance from its distal end and two hinged semicircular portions 322 at its distal end. In the position shown in FIG. 12A the sleeve 320 is in an extended position so that the flared end 146 of the work tip pushes the hinged portions of the sleeve aside. See the schematic view of FIG. 12C which shows that the curved parts of the semicircular portions 322 are fastened to the sleeve by a spring 321. In this position normal phacoemulsification can take place in which cataract tissue impacted by ultrasonic vibration is aspirated into opening 143 of flared portion 146.

When it is time for cleanup, the surgeon can use the finger portion 302 to slide or retract the sleeve. When this is done, the hinged semicircular portions 322 close off the work tip opening as shown in FIGS. 12B and 12D. The sleeve 320 has an opening 330 in it and as mentioned above the flared part has a lateral opening 150. In the retracted position aspiration fluid is sucked into the lateral opening 150. Because in this position the opening 330 and the hole 150 are generally aligned as shown in FIG. 12B, opening 330 acts as the I/A opening during clean up. While the opening 330 is shown with a semicircular shape, it can be provided with any convenient and useful shape. It can also include a plurality of openings in different patterns and sizes. The surgeon will select the adapter to best meet the conditions that are present during the surgery.

Figure 13B:
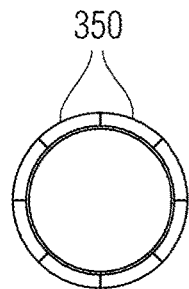
FIG. 13B is a plan view of the adapter of FIG. 13A.
Figure 13D:
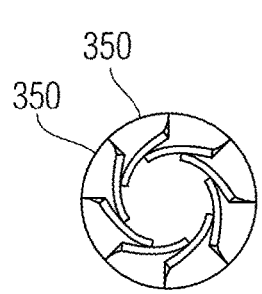
FIG. 13D is a plan view of FIG. 13C.
Figure 13F:
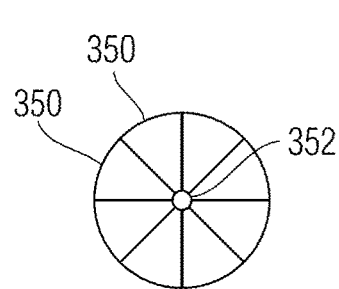
FIG. 13F is a plan view of FIG. 13E.
Figure 13A:
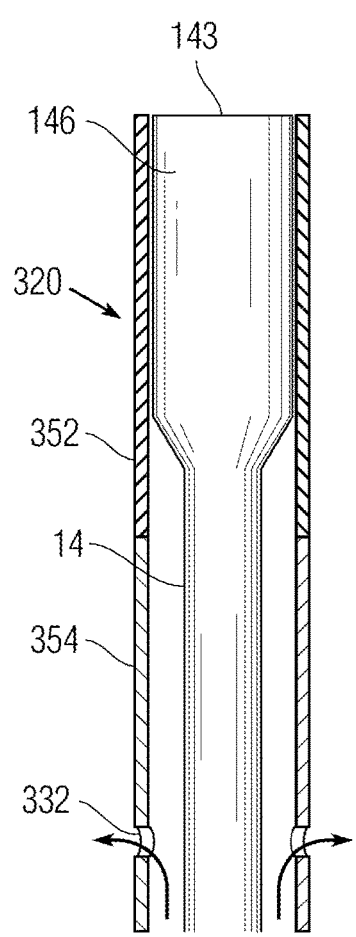
FIG. 13A is a cross sectional elevation view of an adapter in the form of a flexible folding sleeve according to the present invention mounted on a work tip in an open position.

An alternative embodiment of a slidable sleeve 320 that can be configured for I/A clean up is shown in FIG. 13A in cross section located about a work tip with a flared part 146. The sleeve has a proximal part 354 and a distal part 352, with irrigation holes 332 located in the proximal part. At least the distal end of the part 352 is in the form of multiple (e.g., 8) segments 350 designed to naturally fold over the opening 143 of the work tip. Compare FIGS. 13B, 13D and 13F. In FIG. 13B the segments are fully retracted. In FIG. 13D the segments are shown as a twisting closure like the diaphragm of a camera. However, they could alternatively be segments of a hemisphere which are not quite together (not shown). FIG. 13F show a complete closure where the segments are segments of a hemisphere which are fully closed (folded) over the opening 143 in the work tip.

Figure 13C:
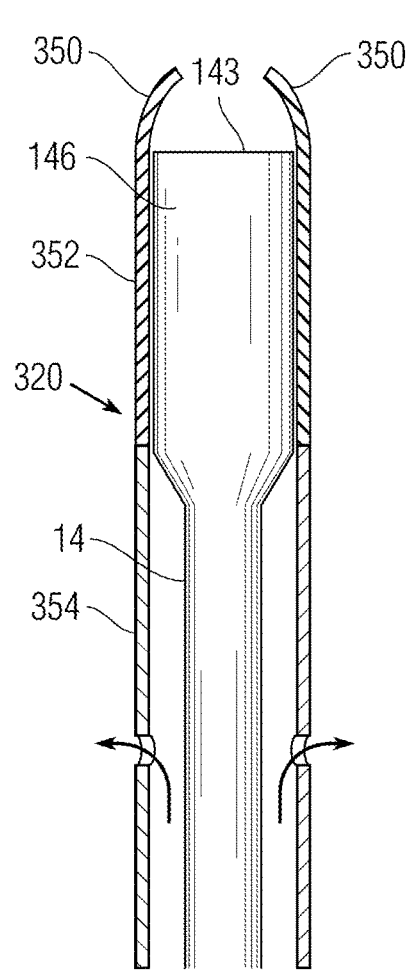
FIG. 13C is a cross sectional elevation view of the adapter of FIG. 13A with the sleeve moved upward to partially close the end of the work piece.
Figure 13E:
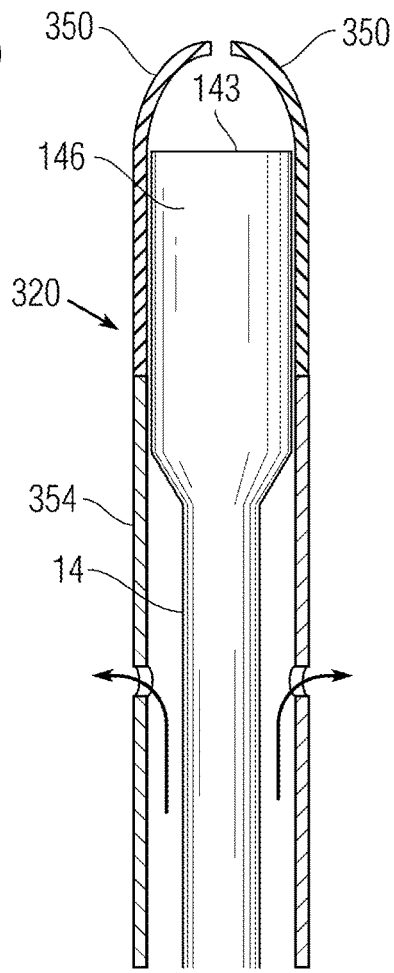
FIG. 13E is a cross sectional elevation view of the adapter of FIG. 13A with the sleeve moved upward to nearly completely close the end of the work piece.

FIG. 13A shows the sleeve 320 in its retracted position. In that position the flared end 146 is used in its normal phacoemulsification function. Irrigation fluid can flow and exit conventional sleeve 17, so long as adapter sleeve 320 does not block the flow. Where the sleeve 320 is used in place of the end of sleeve 17, the holes 232 in that sleeve provide irrigation fluid. When the finger portion 302 is pushed forward, the sleeve is caused to extend beyond the flared portion 146 as shown in FIG. 13C. As a result, the segments 350 begin the fold toward each other partially closing the opening 143 in flared part 146 as described above. See FIG. 13D.

When sleeve 320 is fully extended, the segments 350 can completely close the opening 143 in flared part 146 or they may leave a small opening 352 that can be used for I/A clean up.

Figure 14A:
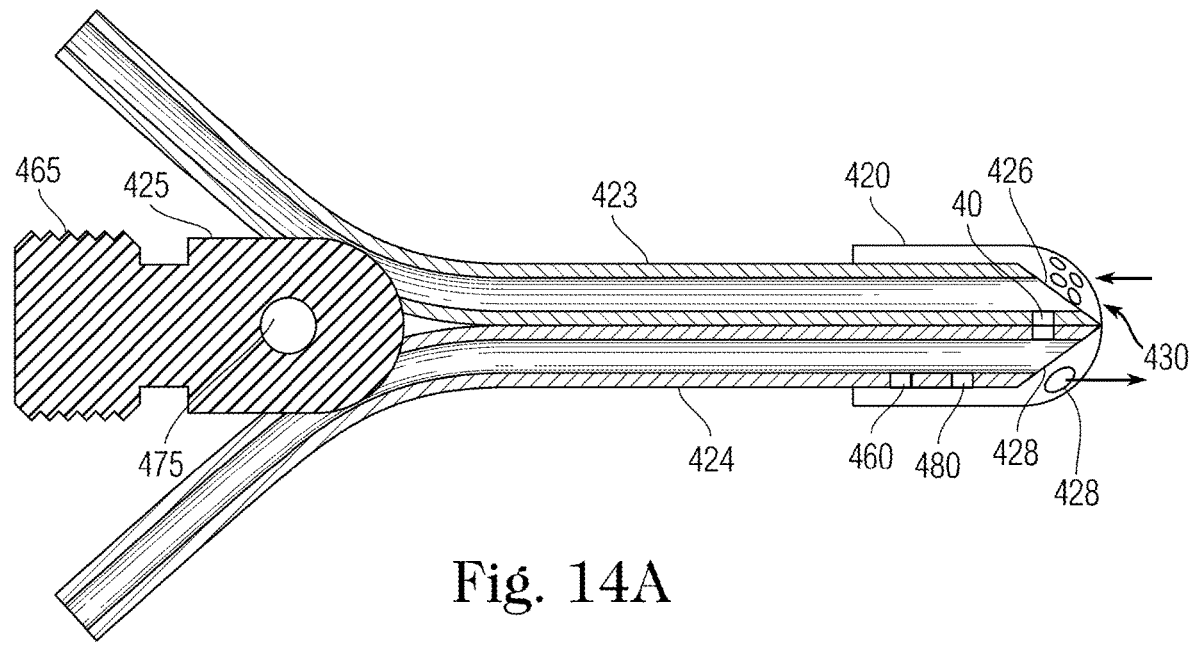
FIG. 14A is a cross-sectional view of a dual lumen work tip with an adapter according the present invention installed at the distal end.

FIG. 14A shows a dual lumen work tip of a type disclosed in the present inventor's U.S. Published Patent Application No. 2016/0106580 A1, which is incorporated herein by reference in its entirety. This work tip has two tubes 423 and 424 joined together at hub 425 and at various sections where the tubes come in contact with each other. The entire assembly can be connected with thread 465 to an ultrasonic hand piece. Depending on the preference of the surgeon, either one of the two tubes or both of the tubes can irrigate the surgical site or aspirate tissue and fluid from the surgical site. If both tubes aspirate through openings 426 and 428 then a separate infusion source needs to be provided. The dual lumen tip and hub can be tightened onto the hand piece with a wrench designed to be inserted into opening 475.

Figure 14B:
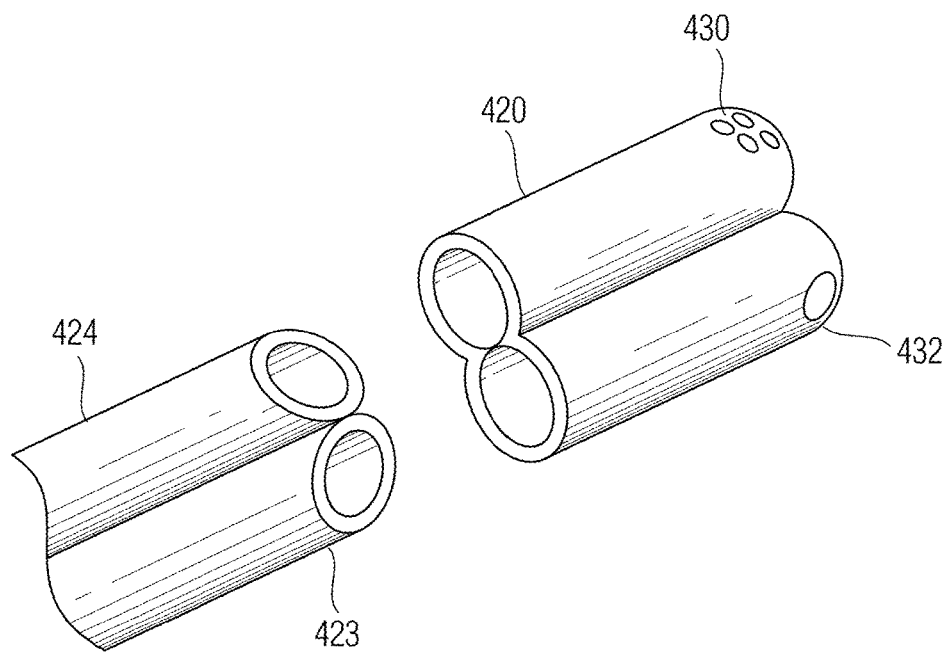
FIG. 14B shows a perspective view of the distal end of the work tip and the adapter prior to installation over the distal end.

In a typical phacoemulsification operation with the work tip of FIG. 14A, irrigation fluid is directed to the cataract through tube 424 to opening 428 and ports 460, 480. Tissue is aspirated through opening 426 into tube 423. As one aspect of the present invention, I/A clean up can be improved with this instrument by placing an adapter sleeve 420 over the distal ends of the tubes 423, 424. This adapter 420 is shown prior to installation in FIG. 14B. The adapter when installed blocks the irrigation and aspiration flow paths of the work tip through openings 426, 428, 460 and 480. In their place a plurality of aspiration holes 430 are provided in the adapter 420. Also, irrigation is limited to hole 432 in the adapter.

With this design, the dual lumen work tip is removed from the eye. Then the adapter is placed on the work tip and retained there by any of the methods shown in FIGS. 5B, 6, 7A, 8B, 9B and 10. Finally the work tip is returned to the eye to complete the I/A clean up. However, the adapter 420 can be modified to have a shape like that in FIG. 12 or 13 so that it can be withdrawn from the distal end during phacoemulsification and extended during the subsequent clean up. During this extension a portion of the sleeve would extend over the openings 426, 428 in the distal ends of the tubes 423, 424 as shown in FIGS. 12 and 13. The extension and retraction of the sleeve 420 can be by way of a mechanism 300 shown in FIG. 11.

While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. An adapter for an ultrasonic surgical hand piece having a single lumen work tip with a cutting edge at the distal end of the work tip adapted to break up tissue at its distal end by phacoemulsification, said adapter being designed to adapt the work tip to infusion/aspiration (I/A) cleanup of lens epithelial cells in a capsular bag of an eye of a patient after phacoemulsification, said adapter comprising a one-piece sleeve adapted to be joined to the distal end of the work tip and to cover the cutting edge, said sleeve having a proximal end for removably attaching the adapter to the distal end of the work tip and a smooth cylindrical side surface connected to a distal end that has an external continuously curved smooth surface that smoothly joins its side surface, a most distal portion of the sleeve having a uniform thickness greater than the proximal end of the sleeve, and at least one aspiration hole that extends through the thicker most distal portion of the sleeve and at a location more distal than the distal end of the work tip when the adapter is joined to the work tip.

2. The adapter according to claim 1 wherein the sleeve is sized to fit within an opening in the distal end of the work tip, the sleeve includes at least one protrusion on its exterior surface near its distal end and wherein the work tip has at least one recess in its interior surface that engages the sleeve protrusion to hold the adapter on the work tip.

3. The adapter according to claim 1 wherein the sleeve is sized to fit within an opening in the distal end of the work tip, the diameter of the sleeve with respect to the opening in the distal end is such that the adapter becomes press fit in the work tip, and the sleeve further including a raised portion on its distal end that has the same diameter as the work tip so that the outer surfaces of the work tip and the adapter join when the adapter is installed on the work tip, the aspiration hole being located in the raised portion of the sleeve.

4. The adapter according to claim 1 wherein the sleeve is sized to fit about an opening in the distal end of the work tip, the sleeve includes threads on its interior surface at its proximal end, and wherein the work tip includes threads on its exterior surface, and wherein the sleeve threads engage the work tip threads to hold the adapter on the work tip.

5. The adapter according to claim 1 wherein the sleeve is sized to fit about an opening in the distal end of the work tip, the sleeve includes an inwardly tapered edge at its proximal end, at least one of said sleeve or sleeve edge being flexible so as to expand outwardly, and wherein the work tip has a recess at a distance from its distal end, and wherein the sleeve flexible edge can be passed over the work tip to engage the recess and hold the adapter on the work tip.

6. An adapter for an ultrasonic surgical hand piece having a single lumen work tip with a cutting edge at a distal end of the work tip adapted to break up tissue at its distal end by phacoemulsification, said adapter being designed for reversibly adapting the work tip to perform an aspiration-infusion function after phacoemulsification, said adapter comprising a one-piece sleeve adapted to be joined to the distal end of the work tip and to cover the cutting edge, said sleeve having a proximal end for removably attaching the adapter to the distal end of the work tip and a smooth cylindrical side surface connected to a distal end that has an external continuously curved smooth surface that smoothly joins its side surface and a most distal portion having a uniform thickness greater than the proximal end of the sleeve, and at least one aspiration hole that extends through the thicker most distal portion of the sleeve and at a location more distal than the distal end of the work tip when the adapter is joined to the work tip.

7. The adapter of claim 6 wherein the hand piece is adapted for irrigation/aspiration (I/A) cleanup of lens epithelial cells in a capsular bag of an eye of a patient after phacoemulsification.

8. The adapter of claim 6 wherein the hand piece is adapted for the removal of neurological tissue.

9. An adapter for a surgical hand piece having a single lumen work tip with a distal end to perform tissue emulsification by phacoemulsification, said adapter being designed to convert the work tip from phacoemulsification cutting to infusion/aspiration (I/A) cleanup after tissue emulsification and back again by removably attaching and removing, respectively, the adapter from the work tip, said adapter comprising a one-piece sleeve adapted to be removably joined to the distal end of the work tip, said sleeve having a proximal end for removably attaching the adapter to the distal end of the work tip and a smooth cylindrical side surface connected to a distal end of the sleeve having an external continuously curved smooth surface that joins smoothly its side surface, a most distal portion of the sleeve having a uniform thickness greater than the proximal end of the sleeve, and at least one aspiration hole that extends through the thicker most distal portion of the sleeve and at a location more distal than the distal end of the work tip when the adapter is joined to the work tip.

* * * * *